(12) United States Patent
Martinez et al.

(10) Patent No.: US 7,582,801 B2
(45) Date of Patent: Sep. 1, 2009

(54) SYNTHESIS OF [1-$^{13}$C]PYRUVIC ACID], [2-$^{13}$C]PYRUVIC ACID], [3-$^{13}$C]PYRUVIC ACID] AND COMBINATIONS THEREOF

(75) Inventors: Rodolfo A. Martinez, Santa Fe, NM (US); Clifford J. Unkefer, Los Alamos, NM (US); Marc A. Alvarez, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 389 days.

(21) Appl. No.: 11/052,589

(22) Filed: Feb. 7, 2005

(65) Prior Publication Data

US 2006/0178534 A1    Aug. 10, 2006

(51) Int. Cl.
C07C 49/04    (2006.01)
(52) U.S. Cl. .................. 568/308; 568/328; 436/128; 424/1.37
(58) Field of Classification Search .......... 568/308, 568/328; 424/1.37; 436/128
See application file for complete search history.

(56) References Cited

U.S. PATENT DOCUMENTS 3,700,772 A * 10/1972 Addor et al. ............... 514/128
3,910,955 A * 10/1975 Chapman et al. ............ 549/49

OTHER PUBLICATIONS

Martinez et al, Organic Process Research & Development, 2002, 6, 851-854.*
Choudhry et al, J. Org. Chem., 1989, 54, 3755-3757.*

* cited by examiner

*Primary Examiner*—Shailendra Kumar
(74) *Attorney, Agent, or Firm*—Bruce H. Cottrell

(57) ABSTRACT

The present invention is directed to labeled compounds, of the formulae

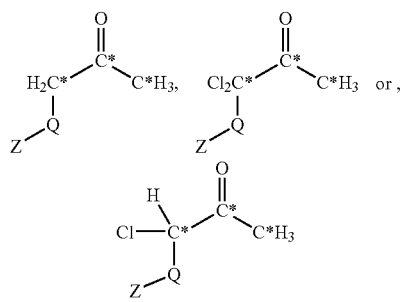

wherein C* is each independently selected from the group consisting of $^{13}$C and $^{12}$C with the proviso that at least one C* is $^{13}$C, each hydrogen of the methylene group can independently be either hydrogen or deuterium, the methyl group includes either zero or three deuterium atoms, Q is from the group of sulfide, sulfinyl, and sulfone, Z is an aryl group from the group of 1-naphthyl, substituted 1-naphthyl, 2-naphthyl, substituted 2-naphthyl, and phenyl groups with the structure

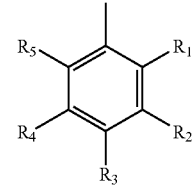

wherein $R_1$, $R_2$, $R_3$, $R_4$ and $R_5$ are each independently from the group of hydrogen, a $C_1$-$C_4$ lower alkyl, a halogen, and an amino group from the group of $NH_2$, NHR and NRR' where R and R' are each independently from the group of a $C_1$-$C_4$ lower alkyl, a phenyl, and an alkoxy group, and the methyl group can include either zero or three deuterium atoms.

5 Claims, 1 Drawing Sheet

SYNTHESIS OF [1-$^{13}$C]PYRUVIC ACID], [2-$^{13}$C]PYRUVIC ACID], [3-$^{13}$C]PYRUVIC ACID] AND COMBINATIONS THEREOF

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to labeled compounds and more particularly to compounds labeled with carbon-13 and hydrogen-2.

BACKGROUND OF THE INVENTION

The use of isotopically labeled pyruvic acid is presently under study for use in medical diagnostics. Pyruvic acid is also known by the IUPAC name of propanoic acid, 2-oxo. For example, U.S. Published Patent Application 2003/0148533 describe $^{13}$C-labeled pyruvic acid as a Krebs cycle metabolite precursor for studies of metabolic fluxes in target organisms and U.S. Pat. No. 6,329,208 describe use of $^{13}$C-labeled pyruvate in metabolic studies. There is a current need in preclinical trials for around 400 grams per year of isotopically labeled pyruvic acid. A projected quantity of over 500,000 grams per year is expected following potential approval. Unfortunately, the currently available [1-$^{13}$C]pyruvic acid is quite expensive. For the diagnostic approach to find wide usage, new synthetic routes to [1-$^{13}$C]pyruvic acid as well as [2-$^{13}$C]pyruvic acid and [3-$^{13}$C]pyruvic acid are needed.

SUMMARY OF THE INVENTION

In accordance with the purposes of the present invention, as embodied and broadly described herein, the present invention provides a labeled compound of the formula

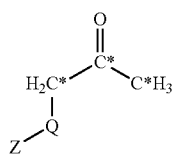

wherein C* is each independently selected from the group consisting of $^{13}$C and $^{12}$C with the proviso that at least one C* is $^{13}$C, the methylene group includes zero, one or two deuterium atoms, the methyl group includes either zero or three deuterium atoms, Q is selected from the group consisting of sulfide, sulfinyl, and sulfone, and Z is an aryl group selected from the group consisting of 1-naphthyl, substituted 1-naphthyl, 2-naphthyl, substituted 2-naphthyl, and phenyl groups with the structure

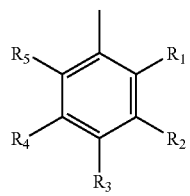

wherein $R_1$, $R_2$, $R_3$, $R_4$ and $R_5$ are each independently selected from the group consisting of hydrogen, a $C_1$-$C_4$ lower alkyl, a halogen, and an amino group selected from the group consisting of $NH_2$, NHR and NRR' where R and R' are each independently selected from the group consisting of a $C_1$-$C_4$ lower alkyl, a phenyl, and an alkoxy group.

The present invention further provides a labeled compound of the formula

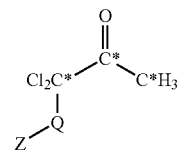

wherein C* is each independently selected from the group consisting of $^{13}$C and $^{12}$C with the proviso that at least one C* is $^{13}$C, the methyl group includes either zero or three deuterium atoms, Q is selected from the group consisting of sulfide, sulfinyl, and sulfone, and Z is an aryl group selected from the group consisting of 1-naphthyl, substituted 1-naphthyl, 2-naphthyl, substituted 2-naphthyl, and phenyl groups with the structure

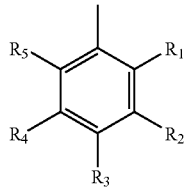

wherein $R_1$, $R_2$, $R_3$, $R_4$ and $R_5$ are each independently selected from the group consisting of hydrogen, a $C_1$-$C_4$ lower alkyl, a halogen, and an amino group from the group consisting of $NH_2$, NHR and NRR' where R and R' are each independently selected from the group consisting of a $C_1$-$C_4$ lower alkyl, a phenyl, and an alkoxy group.

The present invention further provides a labeled compound of the formula

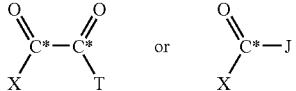

where X is from the group of —$NR_6R_7$ and —$OR_8$ where $R_6$ and $R_7$ are each independently selected from the group of $C_1$-$C_4$ lower alkyl, alkoxy and aryl and $R_8$ is from the group of $C_1$-$C_4$ lower alkyl, alkoxy and aryl, T is from the group of —$CH_3$, —$CD_3$, —$CH_2$—S—$R_9$, —$CH_2$—S(O)—$R_9$, and —$CH_2$—(O)S(O)—$R_9$, J is from the group of —CH(OH)—$CH_2$—S—$R_9$, —CH(OH)—$CH_2$—S(O)—$R_9$, and —CH(OH)—$CH_2$—(O)S(O)—$R_9$ where $R_9$ is an aryl group from the group of 1-naphthyl, substituted 1-naphthyl, 2-naphthyl, substituted 2-naphthyl, and phenyl groups with the structure

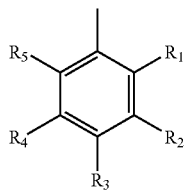

wherein $R_1$, $R_2$, $R_3$, $R_4$ and $R_5$ are each independently from the group of hydrogen, a $C_1$-$C_4$ lower alkyl, a halogen, and an amino group from the group of NH2, NHR and NRR' where R and R' are each independently from the group of a $C_1$-$C_4$ lower alkyl, a phenyl, and an alkoxy group, and C* are each independently selected from the group consisting of $^{13}C$ and $^{12}C$ with the proviso that at least one C* is $^{13}C$.

Th present invention still further provides processes of preparing the various compounds of the present invention.

DETAILED DESCRIPTION

Figure 1:
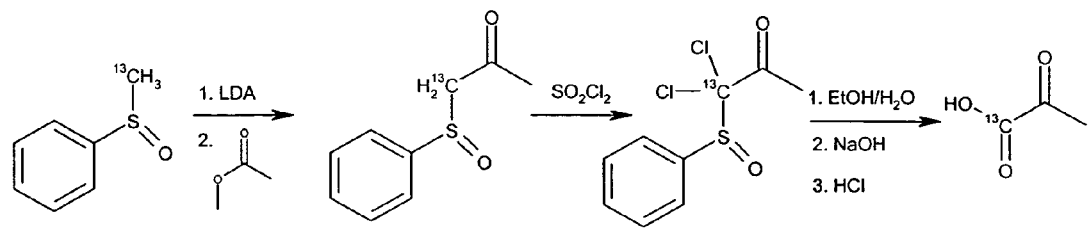
FIG. 1 shows a synthetic route to [1-$^{13}$C]pyruvic acid through the intermediate compounds of α-(phenyl sulfinyl) [1-$^{13}$C]acetone and 1,1-dichloro-1-(phenylsulfinyl)[1-$^{13}$C] acetone.

The present invention is concerned with various labeled compounds useful for the ultimate preparation of the labeled compounds, [1-$^{13}$C]pyruvic acid, [2-$^{13}$C]pyruvic acid and [3-$^{13}$C]pyruvic acid and the like, and/or preparation of other interesting products and to processes of preparing such labeled compounds.

As used herein, the term "aryl" means a monovalent monocyclic or bicyclic aromatic hydrocarbon radical of 6 to 10 ring atoms, and optionally substituted independently with one, two, three, four or five substituents selected from alkyl, haloalkyl, cycloalkyl, halo, nitro, cyano, —OR (where R is hydrogen, alkyl, haloalkyl, cycloalkyl, optionally substituted phenyl), acyl, and —COOR (where R is hydrogen or alkyl). More specifically, the term "aryl" includes, but is not limited to, 1-naphthyl, substituted 1-naphthyl, 2-naphthyl, substituted 2-naphthyl, and phenyl groups with the structure

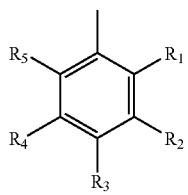

wherein $R_1$, $R_2$, $R_3$, $R_4$ and $R_5$ are each independently a lower alkyl, i.e., a $C_1$-$C_4$ alkyl such as methyl, ethyl, n-propyl, iso-propyl, butyl, isobutyl, and tert-butyl, a halogen such as chloro, bromo or iodo, an amino group such as NH$_2$, NHR or NRR' where R and R' are each a lower alkyl or aryl as described above, or an alkoxy group such as O-alkyl or O-aryl where the alkyl is a lower alkyl as described above or an aryl as described above. By "substituted" is meant that the naphthyl group can include one or more substituents in place of a hydrogen atom, such substituents including the same as described for $R_1$-$R_5$.

Selected embodiments of the present invention include labeled compounds of the formula

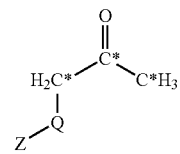

wherein C* is each independently selected from the group consisting of $^{13}C$ and $^{12}C$ with the proviso that at least one C* is $^{13}C$, the methylene group includes zero, one or two deuterium atoms, the methyl group includes either zero or three deuterium atoms, Q is selected from the group consisting of sulfide, sulfinyl, and sulfone, and Z is an aryl group selected from the group consisting of 1-naphthyl, substituted 1-naphthyl, 2-naphthyl, substituted 2-naphthyl, and phenyl groups with the structure

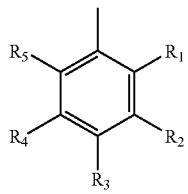

wherein $R_1$, $R_2$, $R_3$, $R_4$ and $R_5$ are each independently selected from the group consisting of hydrogen, a $C_1$-$C_4$ lower alkyl, a halogen, and an amino group selected from the group consisting of NH$_2$, NHR and NRR' where R and R' are each independently selected from the group consisting of a $C_1$-$C_4$ lower alkyl, a phenyl, and an alkoxy group.

Among particular species with these structures are included α-(arylsulfinyl) [1-$^{13}$C]acetone, α-(arylsulfinyl)[2-$^{13}$C]acetone, α-(arylsulfinyl)[3-$^{13}$C]acetone, α-(arylsulfone)[1-$^{13}$C]acetone, α-(arylsulfone)[2-$^{13}$C]acetone, α-(arylsulfone)[3-$^{13}$C]acetone, α-(arylsulfide)[1-$^{13}$C]acetone, α-(arylsulfide)[2-$^{13}$C]acetone, α-(arylsulfide)[3-$^{13}$C]acetone, α-(arylsulfinyl)[1,2-$^{13}$C]acetone, α-(arylsulfinyl)[2,3-3C]acetone, α-(arylsulfinyl)[1,2,3-$^{13}$C]acetone, α-(arylsulfone)[1,2-$^{13}$C]acetone, α-(arylsulfone)[2,3-$^{13}$C]acetone, α-(arylsulfone)[1,2,3-$^{13}$C]acetone, α-(arylsulfide)[1,2-$^{3}$C]acetone, α-(arylsulfide)[2,3-$^{13}$C]acetone and α-(arylsulfide) [1,2,3-$^{13}$C]. None of these enumerated species include deuterium in place of the hydrogens on the methylene group or deuterium in place of the hydrogens the methyl group. The particular species of the present invention can also include the above compounds and structures where the methylene group includes either one or two deuterium atoms in place of one or two of the hydrogen atoms. Also, the particular species of the present invention can include the above compounds and structures where the methyl group includes three deuterium atoms in place of the three hydrogen atoms of the methyl group.

Availability of these described compounds such as α-(arylsulfinyl)[1-$^{13}$C]acetone, α-(arylsulfinyl)[2-$^{13}$C]acetone, α-(arylsulfinyl)[3-$^{13}$C]acetone, α-(arylsulfinyl)[1,2-$^{13}$C]acetone, α-(arylsulfinyl) [2,3-$^{13}$C]acetone, α-(arylsulfinyl) [1,2,3-$^{13}$C]acetone and the like, optionally where the methylene group includes either zero, one or two deuterium atoms and the methyl group includes either zero or three deuterium atoms will allow researchers to take advantage of the wealth of chemistry that has been done using such unlabeled acetones.

Other embodiments of the present invention also include labeled compounds of the formula

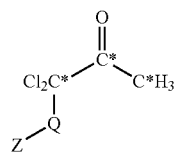

wherein C* is each independently selected from the group consisting of $^{13}$C and $^{12}$C with the proviso that at least one C* is $^{13}$C, the methyl group includes either zero or three deuterium atoms, Q is selected from the group consisting of sulfide, sulfinyl, and sulfone, and Z is an aryl group selected from the group consisting of 1-naphthyl, substituted 1-naphthyl, 2-naphthyl, substituted 2-naphthyl, and phenyl groups with the structure

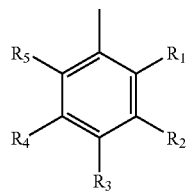

wherein $R_1$, $R_2$, $R_3$, $R_4$ and $R_5$ are each independently selected from the group consisting of hydrogen, a $C_1$-$C_4$ lower alkyl, a halogen, and an amino group from the group consisting of $NH_2$, NHR and NRR' where R and R' are each independently selected from the group consisting of a $C_1$-$C_4$ lower alkyl, a phenyl, and an alkoxy group. Among particular species with these structures are included 1,1-dichloro-1-(arylsulfinyl)[1-$^{13}$C]acetone, 1,1-dichloro-1-(arylsulfinyl)[2-$^{13}$C]acetone, 1,1-dichloro-1-(arylsulfinyl)[3-$^{13}$C]acetone, 1,1-dichloro-1-(arylsulfone)[1-$^{13}$C]acetone, 1,1-dichloro-1-(arylsulfone)[2-$^{13}$C]acetone, 1,1-dichloro-1-(arylsulfone)[3-$^{13}$C]acetone, 1,1-dichloro-1-(arylsulfide)[1-$^{13}$C]acetone, 1,1-dichloro-1-(arylsulfide)[2-$^{13}$C]acetone and 1,1-dichloro-1-(arylsulfide)[3-$^{13}$C]acetone, 1,1-dichloro-1-(arylsulfinyl)[1,2-$^{13}$C]acetone, 1,1-dichloro-1-(arylsulfinyl)[2,3-$^{13}$C]acetone, 1,1-dichloro-1-(arylsulfinyl)[1,2,3 -$^{13}$C]acetone, 1,1-dichloro-1-(arylsulfone)[1,2-$^{13}$C]acetone, 1,1-dichloro-1-(arylsulfone)[2,3-$^{13}$C]acetone, 1,1-dichloro-1-(arylsulfone)[1,2,3-$^{13}$C]acetone, 1,1-dichloro-1-(arylsulfide)[1,2-$^{13}$C]acetone, 1,1-dichloro-1-(arylsulfide)[2,3-$^{13}$C]acetone and 1,1-dichloro-1-(arylsulfide)[1,2,3-$^{13}$C]acetone. None of these enumerated species include deuterium in place of the hydrogens on the methyl group. The particular species of the present invention can also include the above compounds and structures where the methyl group includes three deuterium atoms in place of the three hydrogen atoms of the methyl group.

Availability of these described compounds such as 1,1-dichloro-1-(arylsulfinyl)[1-$^{13}$C]acetone, 1,1-dichloro-1-(arylsulfinyl)[2-$^{13}$C]acetone, 1,1-dichloro-1-(arylsulfinyl)[3-$^{13}$C]acetone, 1,1-dichloro-1-(arylsulfinyl)[1,2-$^{13}$C]acetone, 1,1-dichloro-1-(arylsulfinyl)[2,3-$^{13}$C]acetone, 1,1-dichloro-1-(arylsulfinyl)[1,2,3-$^{13}$C]acetone and the like, optionally where the methyl group includes either zero or three deuterium atoms, will similarly allow researchers to take advantage of the wealth of chemistry that has been done using such unlabeled acetones.

Still other embodiments of the present invention also include labeled compounds of the formula

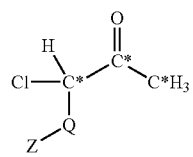

wherein C* is each independently selected from the group consisting of $^{13}$C and $^{12}$C with the proviso that at least one C* is $^{13}$C, the methylene group includes zero or one deuterium atom, the methyl group includes either zero or three deuterium atoms, Q is selected from the group consisting of sulfide, sulfinyl, and sulfone, and Z is an aryl group selected from the group consisting of 1-naphthyl, substituted 1-naphthyl, 2-naphthyl, substituted 2-naphthyl, and phenyl groups with the structure

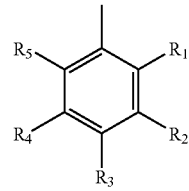

wherein $R_1$, $R_2$, $R_3$, $R_4$ and $R_5$ are each independently selected from the group consisting of hydrogen, a $C_1$-$C_4$ lower alkyl, a halogen, and an amino group from the group consisting of $NH_2$, NHR and NRR' where R and R' are each independently selected from the group consisting of a $C_1$-$C_4$ lower alkyl, a phenyl, and an alkoxy group. Among particular species with these structures are included 1-chloro-1-(arylsulfinyl)[1-$^{13}$C]acetone, 1-chloro-1-(arylsulfinyl)[2-$^{13}$C]acetone, 1-chloro-1-(arylsulfinyl)[3-$^{13}$C]acetone, 1-chloro-1-(arylsulfone)[1-$^{13}$C]acetone, 1-chloro-1-(arylsulfone)[2-$^{13}$C]acetone, 1-chloro-1-(arylsulfone)[3-$^{13}$C]acetone, 1-chloro-1-(arylsulfide)[1-$^{13}$C]acetone, 1-chloro-1-(arylsulfide)[2-$^{13}$C]acetone, 1-chloro-1-(arylsulfide)[3-$^{13}$C]acetone, 1-chloro-1-(arylsulfinyl)[1,2-$^{13}$C]acetone, 1-chloro-1-(arylsulfinyl)[2,3-$^{13}$C]acetone, 1-chloro-1-(arylsulfinyl)[1,2,3-$^{13}$C]acetone, 1-chloro-1-(arylsulfone)[1,2-$^{13}$C]acetone, 1-chloro-1-(arylsulfone)[2,3-$^{13}$C]acetone, 1-chloro-1-(arylsulfone)[1,2,3-$^{13}$C]acetone, 1-chloro-1-(arylsulfide)[1,2-$^{13}$C]acetone, 1-chloro-1-(arylsulfide)[2,3-$^{13}$C]acetone and 1-chloro-1-(arylsulfide)[1,2,3-$^{13}$C]acetone. None of these enumerated species include deuterium in place of the hydrogen on the methylene group or deuterium in place of the hydrogens on the methyl group. The particular species of the present invention can also include the above compounds and structures where the methylene group includes a deuterium atom in place of the hydrogen atom. Also, the methyl group can include three deuterium atoms in place of the three hydrogen atoms of the methyl group.

Availability of these described compounds such as 1-chloro-1-(arylsulfinyl)[1-$^{13}$C]acetone, 1-chloro-1-(arylsulfinyl)[2-$^{13}$C]acetone, 1-chloro-1-(arylsulfinyl)[3-$^{13}$C]acetone, 1-chloro-1-(arylsulfinyl)[1,2-$^{13}$C]acetone, 1-chloro-1-(arylsulfinyl)[2,3-$^{13}$C]acetone, 1-chloro-1-(arylsulfinyl)[1,2,3-$^{13}$C]acetone and the like, optionally where the methylene group includes either zero or one deuterium atoms and the methyl group includes either zero or three deuterium atoms, will similarly allow researchers to take advantage of the wealth of chemistry that has been done using such unlabeled acetones.

Still other embodiments of the present invention include labeled compounds of the formula

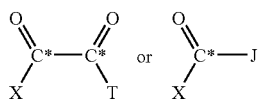

where X is from the group of —NR$_6$R$_7$ and —OR$_8$ where R$_6$ and R$_7$ are each independently selected from the group of C$_1$-C$_4$ lower alkyl, alkoxy and aryl and R$_8$ is from the group of C$_1$-C$_4$ lower alkyl, alkoxy and aryl, T is from the group of —CH$_3$, —CD$_3$, —CH$_2$—S—R$_9$, —CH$_2$—S(O)—R$_9$, and —CH$_2$—(O)S(O)—R$_9$, J is from the group of —CH(OH)—CH$_2$—S—R$_9$, —CH(OH)—CH$_2$—S(O)—R$_9$, and —CH(OH)—CH$_2$—(O)S(O)—R$_9$ where R$_9$ is an aryl group from the group of 1-naphthyl, substituted 1-naphthyl, 2-naphthyl, substituted 2-naphthyl, and phenyl groups with the structure

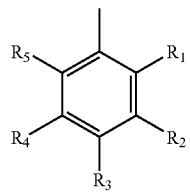

wherein R$_1$, R$_2$, R$_3$, R$_4$ and R$_5$ are each independently from the group of hydrogen, a C$_1$-C$_4$ lower alkyl, a halogen, and an amino group from the group of NH$_2$, NHR and NRR' where R and R' are each independently from the group of a C$_1$-C$_4$ lower alkyl, a phenyl, and an alkoxy group, and C* are each independently selected from the group consisting of $^{13}$C and $^{12}$C with the proviso that at least one C* is $^{13}$C. Among particular species with these structures are included propanamide-1-$^{13}$C,N,N,dimethyl, 3-[phenylthio]-2-oxo-, propanamide-1-$^{13}$C,N,N-dimethyl-α-hydroxy-β-(phenylsulfonyl), propanamide-, 1-$^{13}$C, N,N-dimethyl-2-oxo- and the like. Availability of these compounds will similarly allow researchers to take advantage of the wealth of chemistry that has been done using such unlabeled small molecules.

The present invention is more particularly described in the following examples which are intended as illustrative only, since numerous modifications and variations will be apparent to those skilled in the art.

EXAMPLE 1

Synthesis of isotopically labeled α-(phenyl sulfinyl)[1-$^{13}$C]acetone was as follows. Benzene, (methyl-$^{13}$C-sulfinyl) (4.28 grams (g), 0.03 moles) was dissolved into tetrahydrofuran (THF) (42 milliliters (ml). This solution was cooled to −78° C. with a dry ice/isopropanol bath. To the cooled solution, lithium diisopropylamide (2M, 32 ml, 0.064 moles) was added slowly. Methyl acetate (2.25 g, 0.03 moles) was added neat to the reaction. The reaction was stirred at −78° C. for 1 hour and then the ice bath was removed. The reaction mixture was stirred overnight at room temperature. Water (40 ml) was added to the reaction mixture and the mixture was adjusted to pH 2.5 by addition of (1M) hydrochloric acid. The resultant product was extracted with three 100 ml portions of ethyl acetate. The organic layer was dried over sodium sulfate (Na$_2$SO$_4$) and then evaporated to give a crude yield of 6.02 g. The crude product was dissolved into dichloromethane (60 ml) and this was extracted with three 100 ml portions of 1 M aqueous sodium hydroxide. The layers were separated and the aqueous base phase was acidified to pH 2.5 by addition of hydrochloric acid. The aqueous layer was extracted with three 60 ml portions of dichloromethane, dried over sodium sulfate and evaporated to yield 4.8 g of α-(phenyl sulfinyl) [1-$^{13}$C]acetone. The product was used in the subsequent reaction without further purification.

EXAMPLE 2

Synthesis of [1-$^{13}$C] propanoic acid, 2-oxo-, ethyl ester and [1-$^{13}$C]propanoic acid, 2-oxo- were as follows from α-(phenyl sulfinyl)[1-$^{13}$C]acetone from Example 1. The α-(phenyl sulfinyl) [1-$^{13}$C]acetone (4.5 g, 0.024 moles) was dissolved into dichloromethane (45 ml)and to this sulfuryl chloride (6.96 g, 0.051 moles) was added slowly. The 1,1-dichloro-1-(phenylsulfinyl)[1-$^{13}$C]acetone was formed in about 1 hour. The solvent was evaporated and to the residue was added ethanol/water (90/10, 45 ml) and the reaction mixture was heated to reflux for 12 hours. After this period the reaction showed a mixture of 80% [1-$^{13}$C]propanoic acid, 2-oxo-, ethyl ester and 20% [1-$^{13}$C]propanoic acid, 2-oxo-. This material was treated with (1M) hydrochloric acid (60 mL) and heated to give a sole product of the [1-$^{13}$C]propanoic acid, 2-oxo-. The [1-$^{13}$C]propanoic acid, 2-oxo- was dissolved into water and the pH adjusted to about 6.3 by addition of 1M sodium hydroxide. The water was evaporated and then ethanol was added to the solid residue. This was evaporated to yield dry [1-$^{13}$C]propanoic acid, 2-oxo-, sodium salt.

EXAMPLE 3

Figure 2:
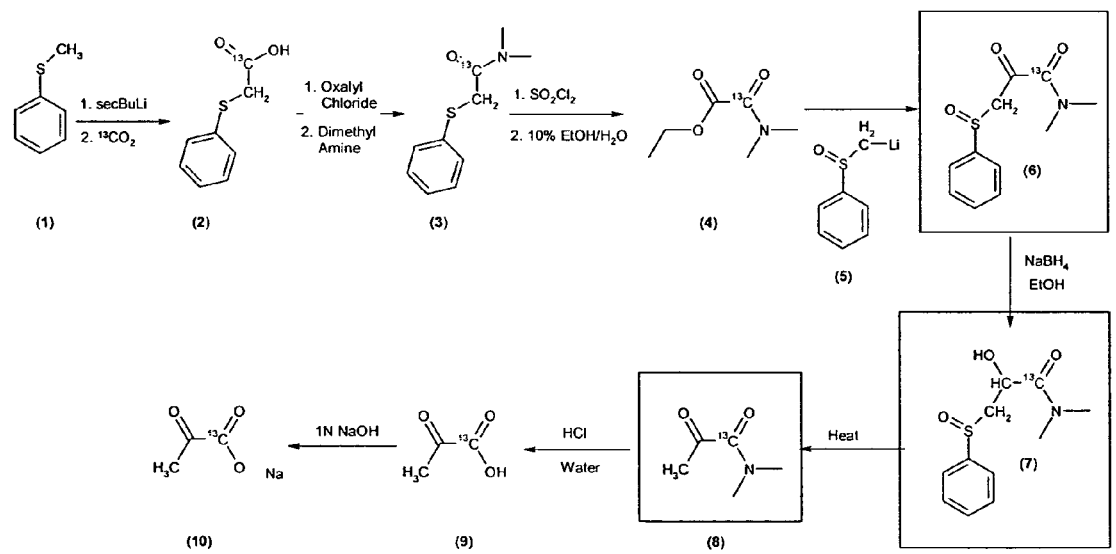
FIG. 2 shows another synthetic route to [1-$^{13}$C]pyruvic acid through the intermediate compounds of [1-$^{13}$C]propanamide, N,N,dimethyl,3-[phenylthio]-2-oxo- and [1-$^{13}$C]propanamide, N,N-dimethyl-α-hydroxy-β-(phenylsulfonyl) and [1-$^{13}$C]propanamide, N,N-dimethyl-2-oxo-.

Synthesis of [1-$^{13}$C]propanamide, N,N,dimethyl,3-[phenylthio]-2-oxo- (compound 6 in FIG. 2) was as follows. Methyl phenyl sulfoxide (4.02 g, 0.0287 moles), prepared in accordance with the description of U.S. Pat. No. 6,753,446, was dissolved into THF (60 mL). This solution was cooled to −78° C. and to it was added lithium diisopropyl amide (1.5M, 21.0 mL 0.0316 moles). The mixture was stirred for 1 hour and then [2-$^{13}$C]acetic acid, 2-(dimethylamino)-2-oxo-, ethyl ester (5 g, 0.0287 moles) was added. The cooling bath was removed and the reaction was allowed to come to room temperature. The reaction was complete after 3 hours and was then treated with aqueous HCl (1M, about 20-30 mL). The reaction mixture was then extracted with ethyl acetate (3×100 mL) and the organic was dried over sodium sulfate and evaporated to give 5.51 g of product. The product was purified by dry column chromatography using an ethyl acetate/hexane mixture (70:30 v/v).

EXAMPLE 4

Synthesis of [1-$^{13}$C]propanamide, N,N-dimethyl-α-hydroxy-β-(phenylsulfonyl) (compound 7 in FIG. 2) was as follows. The [1-$^{13}$C]propanamide, N,N,dimethyl,3-[phenylthio]-2-oxo- from example 3 (5.51 g, 0.0206 moles) was dissolved into ethanol (50 mL). This solution was cooled in an ice bath and to it was added sodium borohydride (0.78 g, 0.0206 moles) which had been dissolved in water (15 mL). The reaction was stirred for 1 hour and then acidified to pH 3 (using 1M HCl) and extracted with ethyl acetate to yield the compound of [1-$^{13}$C]propanamide, N,N-dimethyl-α-hydroxy-β-(phenylsulfonyl) in quantitative yield. The product was used in the subsequent reaction with purification.

EXAMPLE 5

Synthesis of [1-$^{13}$C]propanamide, N,N-dimethyl-2-oxo- (compound 8 in FIG. 2) was as follows. The propanamide, N,N-dimethyl-α-hydroxy-β-(phenylsulfonyl) from example 4 was heated to 100° C. as a neat solid and the product of [1-$^{13}$C]propanamide, N, N-dimethyl-2-oxo- was distilled over under vacuum. Product yield was 80%.

EXAMPLE 6

Synthesis of [1-$^{13}$C]propanoic acid, 2-oxo- (compound 9 in FIG. 2) was as follows. The [1-$^{13}$C]propanamide, N,N-dimethyl-2-oxo- (1 g) was hydrolyzed to the compound of [1-$^{13}$C]propanoic acid, 2-oxo- by heating to reflux in 1M hydrochloric acid (15 mL). Product yield was 93%.

Although the present invention has been described with reference to specific details, it is not intended that such details should be regarded as limitations upon the scope of the invention, except as and to the extent that they are included in the accompanying claims.

What is claimed is:
1. A labeled compound of the formula

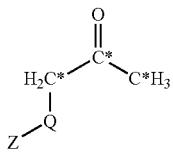

wherein C* is each independently selected from the group consisting of $^{13}$C and $^{12}$C with the proviso that at least one C* is $^{13}$C, the methylene group includes zero, one or two deuterium atoms, the methyl group includes either zero or three deuterium atoms, Q is selected from the group consisting of sulfide, sulfinyl, and sulfone, and Z is an aryl group selected from the group consisting of 1-naphthyl, substituted 1-naphthyl, 2-naphthyl, substituted 2-naphthyl, and phenyl groups with the structure

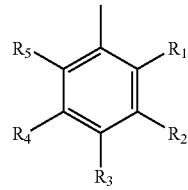

wherein $R_1$, $R_2$, $R_3$, $R_4$ and $R_5$ are each independently selected from the group consisting of hydrogen, a $C_1$-$C_4$ lower alkyl, a halogen, and an amino group selected from the group consisting of $NH_2$, NHR and NRR' where R and R' are each independently selected from the group consisting of a $C_1$-$C_4$ lower alkyl, a phenyl, and an alkoxy group.

2. The compound of claim 1 wherein said Z is selected from the group consisting of phenyl groups with the structure

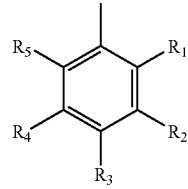

wherein $R_1$, $R_2$, $R_3$, $R_4$ and $R_5$ are each independently selected from the group consisting of hydrogen, a $C_1$-$C_4$ lower alkyl, a halogen, and an amino group from the group consisting of $NH_2$, NHR and NRR' where R and R' are each independently selected from the group consisting of a $C_1$-$C_4$ lower alkyl, a phenyl, and an alkoxy group.

3. The compound of claim 1 wherein Z is phenyl.

4. The compound of claim 1 wherein the methylene group within said compound includes exactly one deuterium atom.

5. The compound of claim 1 wherein said methylene group within said compound includes exactly two deuterium atoms.

* * * * *